(12) United States Patent
Kunz et al.

(10) Patent No.: US 6,171,347 B1
(45) Date of Patent: *Jan. 9, 2001

(54) COMPOSITIONS, METHODS AND KITS FOR REDUCTIVELY REMOVING COLOR FROM DYED HAIR

(75) Inventors: Manuela Kunz; Dominique Le Cruer, both of Marly Schweiz (CH)

(73) Assignee: Wella Aktiengesellschaft, Darmstadt (DE)

( * ) Notice: Under 35 U.S.C. 154(b), the term of this patent shall be extended for 0 days.

This patent is subject to a terminal disclaimer.

(21) Appl. No.: 09/101,099

(22) PCT Filed: Aug. 29, 1997

(86) PCT No.: PCT/EP97/04699

§ 371 Date: Jul. 1, 1998

§ 102(e) Date: Jul. 1, 1998

(87) PCT Pub. No.: WO98/22078

PCT Pub. Date: May 28, 1998

(30) Foreign Application Priority Data

Nov. 16, 1996 (DE) .................................... 196 47 493
Nov. 16, 1996 (DE) .................................... 196 47 494
Apr. 22, 1997 (DE) .................................... 197 16 780

(51) Int. Cl.[7] .............................. A61K 7/13; A61K 7/135
(52) U.S. Cl. .................. 8/407; 8/405; 8/406; 8/431; 8/432; 8/102; 8/107; 8/110; 132/208; 252/188.1; 252/188.2; 252/188.21; 424/62; 424/70.6
(58) Field of Search ................ 8/405, 406, 431, 8/432, 102, 107, 110, 407; 132/208; 424/70.6, 62; 252/188.1, 188.2, 188.21

(56) References Cited

U.S. PATENT DOCUMENTS

| | | | | |
|---|---|---|---|---|
| 4,416,909 | * | 11/1983 | Aversano | 426/265 |
| 4,496,548 | * | 1/1985 | Moldowan et al. | 514/27 |
| 5,332,570 | * | 7/1994 | Bergstrom et al. | 424/72 |
| 5,782,933 | * | 7/1998 | Wis-Surel et al. | 8/431 |

FOREIGN PATENT DOCUMENTS

930581 * 7/1949 (DE) .
1 444 216  11/1968 (DE) .
36 42 097 A1  6/1988 (DE) .
0 310 675 A1  4/1989 (EP) .
0 401 454 A2  12/1990 (EP) .

OTHER PUBLICATIONS

"Grundlagen und Rezepturen der Kosmetika" by Karlheinz Schrader, Huthig Buch Verlag Heidelberg, 1989. (no month available).
English language translation of EP 401,454, Bauer, Dec. 1990.*
English language translation of DE 930,581, Schuberth, May 1951.*
English language translation of FR 2,657,781, L'Oreal, pp. 1–31, Aug. 1991.*
Derwent Abstract of JP 57–007225, Jan. 1982.*
Derwent Abstract of JP 08–175935, Jul. 1996.*
Derwent Abstract of JP 53–029941, Mar. 1978.*
Rompp Chemische Lexicon, 9–th Edition, J. Falbe, M. Regits, Eds., Georg Thieme Press, Stuttgart, New York, pp. 265,266, 4380–4381, 4589–4590 (1989,1991). (no month available).
Stephan Jellinek: "Kosmetologie", 3–rd Edition, Huthig Press, pp. 676 (1976). (no month available).

* cited by examiner

Primary Examiner—Caroline D. Liott
(74) Attorney, Agent, or Firm—Michael J. Striker

(57) ABSTRACT

A multicomponent kit for coloring and later removing color from fibers is described, which consists of a first component and a second component. The first component includes a composition for oxidative dyeing of hair and the second component includes an aqueous or aqueous-alcoholic composition for reductive removal of color from dyed hair. The composition for reductive removal of color from hair has a pH of from 1.8 to 6 and is in the form of a gel, cream, emulsion, foam or solution. It contains from 1 to 50% by weight of one or more reductones, advantageously ascorbic and/or isoascorbic acid or salts thereof, and, in addition to the reductones, from 0.1 to 10% by weight of one or more thiols or a combination of from 0.1 to 10% by weight of one or more thiols and from 0.001 to 5% by weight of one or more sulfites. It also includes one or more pH adjusting agents and standard cosmetic additive ingredients.

21 Claims, No Drawings

COMPOSITIONS, METHODS AND KITS FOR REDUCTIVELY REMOVING COLOR FROM DYED HAIR

BACKGROUND OF THE INVENTION

The subject of the present invention is a multicomponent kit for coloring and later removing color from fibers, especially human hair, which includes both compositions for creating a color on the fiber and compositions for reductive removal of the color.

Oxidative dyes are excellently well suited to covering relatively high proportions of gray; the oxidative dyes used for hair that is up to 50% gray are as a rule called oxidative tints, while the oxidative dyes used for a proportion of up to 100% gray or for "lightening" color are as a rule called oxidative colorings.

Direct dyes, especially nitro dyes, are widely used in nonoxidative dyes (so-called tinting compositions). Because of their small size they can penetrate the hair and color it directly—at least in the outer regions. Such tints are very gentle to the hair and as a rule last through several shampoos.

Direct dyes, especially nitro dyes, are also often used in oxidative dyes for producing certain shades or to intensify the color. It is known that colored polymers created oxidatively in the hair are generally very durable in the presence of such external factors as water, shampoo, or light. Depending on the coloring technique, they are so firmly anchored that they generally remain in the hair until the next time the hair is cut. If removal of the color is desired, then relatively aggressive chemicals must be used, such as formaldehyde sulfoxylates, hydrogen peroxide, or hydrogen peroxide addition products. This does enable extensive color removal but is hazardous to the health or involves hair damage.

Partial removal or stripping of nonoxidative tints is as a rule possible simply by washing the hair several times, but a purposeful, complete, immediate removal of the hair color is not possible in this way.

If a particular hair color is to be worn only for a short period of time, the removal of the hair color under mild, gentle conditions, both in the case of oxidative and nonoxidative colorings, is a problem that has not yet been solved.

SUMMARY OF THE INVENTION

It is an object of the present invention to solve the problem of removal of hair color to be worn for only a short period of time under mild, gentle conditions.

According to the invention, this object is attained by using a combination of a suitable reductone, such as ascorbic acid, and/or a thiol and/or a sulfite.

The use of ascorbic acid in hair care products or hair dyes is known per se. In European Patent EP 0 401 454, for example, it is proposed that residues of hydrogen peroxide that remain in human hair after an oxidative treatment be removed with an aqueous solution of ascorbic acid. Effervescent tablets containing ascorbic acid are suitable for this purpose; they are dissolved in water immediately prior to use and the water is then used to rinse the hair.

Ascorbic acid is also used in Published, Non-Examined German Patent Application DE-OS 1 444 216 in a liquid hair dye, in order to make the otherwise unstable liquid composition durable. The oxidative hair dye of Published, Non-Examined German Patent Application DE-OS 3 642 097 also contains ascorbic acid as a stabilizer. It is all the more surprising that ascorbic acid can advantageously also be used for the reductive removal of oxidative colorings from fibers, such as human hair.

The subject of the present invention is a multicomponent kit for coloring and later removing color from fibers, in particular hair, which is characterized in that it contains, as a component (I), compositions for oxidative or nonoxidative coloring of fibers, in particular human hair, and as component (II), it contains compositions for reductive removal of the color with a content of a reductone and/or a thiol and/or a sulfite.

As a rule, the compositions contained in the multicomponent kit of the invention to create an oxidative color (component (I)) comprise a mixture of two components, namely a chromophore composition, which contains the colorant precursors known as developer substance and coupler substance and optionally contains nonoxidative colorants as well, and an oxidant which is added immediately prior to use to form the oxidative dye, while the composition contained in the multicomponent kit of the invention for creating a nonoxidative color (component (I)) are as a rule present in the form of a single-component preparation.

The multicomponent kit according to the invention contains as a developer substance in the chromophore composition, in the case of the oxidative coloring, at least one colorant precursor suitable for forming oxidative dyes. Especially suitable examples for this purpose are 1,4-diaminobenzene(p-phenylenediamine), 1,4-diamino-2-methylbenzene(p-toluylenediamine), 1,4-diamino-2,6-dimethylbenzene, 1,4-diamino-2,5-dimethylbenzene, 1,4-diamino-2,3-dimethylbenzene, 2-chloro-1,4-diaminobenzene, 4-phenylaminoaniline, 4-dimethylaminoaniline, 4-diethylaminoaniline, 4-[di(2-hydroxyethyl)amino]aniline, 4-[(2-methoxyethyl)amino]aniline, 4-[(3-hydroxypropyl)amino]aniline, 1,4-diamino-2-(2-hydroxyethyl)benzene, 1,4-diamino-2-(1-methylethyl)benzene, 1,3-bis[(4-aminophenyl)(2-hydroxyethyl)amino]-2-propanol, 1,8-bis(2,5-diaminophenoxy)-3,6-dioxaoctane, 4-aminophenol, 4-amino-3-methylphenol, 4-methylaminophenol, 4-amino-2-(aminomethyl)phenol, 4-amino-2-[(2-hydroxyethyl)amino]methylphenol, 4-amino-2-(methoxymethyl)phenol, 4-amino-2-(2-hydroxyethyl)phenol, 5-aminosalicylic acid, 2,5-diaminopyridine, 2,4,5,6-tetraaminopyrimidine, 2,5,6-triamino-4-(1H)-pyrimidone, 4,5-diamino-1-(2-hydroxyethyl)-1H-pyrazole, 4,5-diamino-1-(1-methylethyl)-1H-pyrazole, 4,5-diamino-1-[(4-methylphenyl)methyl]-1H-pyrazole, 1-[(4-chlorophenyl)methyl]-4,5-diamino-1H-pyrazole, 4,5-diamino-1-methyl-1H-pyrazole, and 2-aminophenol, 2-amino-6-methylphenol, 2-amino-5-methylphenol, and/or their salts.

The chromophore composition in the case of the oxidative coloring also contains at least one coupler substance suitable for forming an oxidative color. Examples that can be used for this are aromatic m-diamines, m-aminophenols, polyphenols or naphthols. Especially suitable examples are N-(3-dimethylaminophenyl)urea, 2,6-diaminopyridine, 2-amino-4-[(2-hydroxyethyl)amino]anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl)amino]-1,5-dimethoxybenzene, 2,3-diamino-6-methoxypyridine, 3-amino-6-methoxy-2-(methylamino)pyridine, 2,6-diamino-3,5-dimethoxypyridine, 3,5-diamino-2,6-dimethoxypyridine, 1,3-diaminobenzene, 2,4-diamino-1-(2-hydroxyethoxy)benzene, 1-(2-aminoethoxy)-2,4-diaminobenzene, 2-amino-1-(2-hydroxyethoxy)-4-methylaminobenzene, 2,4- diaminophenoxyacetic acid, 3-[di(2-hydroxyethyl)amino] aniline, 4-amino-2-di[(2-hydroxyethyl)amino]-1-ethoxybenzene, 5-methyl-2-(1-methylethyl)-phenol, 3-[(2-hydroxyethyl)amino]aniline, 3-[(2-aminoethyl)amino] aniline, 1,3-di(2,4-diaminophenoxy)propane, di(2,4-diaminophenoxy)methane, 1,3-diamino-2,4-dimethoxybenzene, 2,6-bis(2-hydroxyethyl)aminotoluene, 4-hydroxyindole, 3-dimethylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methylphenol, 3-amino-2-chloro-6-methylphenol, 3-aminophenol, 2-[(3-hydroxyphenyl)amino]acetamide, 5-[(2-hydroxyethyl)amino]-2-methylphenol, 3-[(2-hydroxyethyl)amino]phenol, 3-[(2-methoxyethyl)amino] phenol, 5-amino-2-ethylphenol, 2-(4-amino-2-hydroxyphenoxy)ethanol, 5-[(3-hydroxypropyl)amino]-2-methylphenol, 3-[(2,3-dihydroxypropyl)amino]-2-methylphenol, 3-[(2-hydroxyethyl)amino]-2-methylphenol, 2-amino-3-hydroxypyridine, 5-amino-4-chloro-2-methylphenol, 1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedioxyaniline, 5-[(2-hydroxyethyl)amino]-1,3-benzodioxol, 6-bromo-1-hydroxy-3,4-methylenedioxybenzene, 3,4-diaminobenzoic acid, 3,4-dihydro-6-hydroxy-1,4(2H)-benzoxazine, 6-amino-3,4-dihydro-1,4(2H)-benzoxazine, 3-methyl-1-phenyl-5-pyrazolone, 5,6-dihydroxyindole, 5,6-dihydroxyindoline, 5-hydroxyindole, 6-hydroxyindole, 7-hydroxyindole, 2,3-indolinedione, and/or their salts.

The developer substances and coupler substances are each contained in the chromophore composition in a quantity of approximately 0.01 to 10 weight % and preferably 0.1 to 5 weight %.

This chromophore composition containing oxidant dyes can also optionally contain in addition nonoxidative dyes (hereinafter called "direct dyes"), such as 1,4-bis[(2-hydroxyethyl)amino]-2-nitrobenzene, 1-(2-hydroxyethyl) amino]-2-nitro-4-[di(2-hydroxyethyl)amino]benzene (HC Blue No. 2), 1-amino-3-methyl-4-[(2-hydroxyethyl)amino]-6-nitrobenzene (HC Violet No. 1), 4-[ethyl-(2-hydroxyethyl)amino]-1-[(2-hydroxyethyl)amino]-2-nitrobenzene hydrochloride (HC Blue No. 12), 4-[di(2-hydroxyethyl)amino]-1-[(2-methoxyethyl)amino]-2-nitrobenzene (HC Blue No. 11), 1-[2,3-dihydroxypropyl) amino]-4-[methyl-(2-hydroxyethyl)amino]-2-nitrobenzene (HC Blue No. 10), 1-[(2,3-dihydroxypropyl)amino]-4-[ethyl-(2-hydroxyethyl)amino]-2-nitrobenzene hydrochloride (HC Blue No. 9), 1-(3-hydroxypropylamino)-4-[di-(2-hydroxyethyl)amino]-2-nitrobenzene (HC Violet No. 2), 1-methylamino-4-[methyl(2,3-dihydroxypropyl)amino-2-nitrobenzene (HC Blue No. 6), 2-((4-amino-2-nitrophenyl) amino)-5-dimethylaminobenzoic acid (HC Blue No. 13), 1-amino-4-[(2-hydroxyethyl)amino]-2-nitrobenzene (HC Red No. 7), 2-amino-4,6-dinitrophenol, 4-amino-2-nitrodiphenylamine (HC Red No. 1), 1-amino-4-[di-(2-hydroxyethyl)amino]-2-nitrobenzene hydrochloride (HC Red No. 13), 1-amino-5-chloro-4-[(2-hydroxyethyl)amino]-2-nitrobenzene, 4-amino-1-[(2-hydroxyethyl)amino]-n-nitrobenzene (HC Red No. 3), 4-amino-3-nitrophenol, 4-[(2-hydroxyethyl)amino]-3-nitrophenol, 1-[(2-aminoethyl) amino]-4-(2-hydroxy)-2-nitrobenzene (HC Orange No. 2), 4-(2,3-dihydroxypropoxy)-1-[(2-hydroxyethyl)amino]-2-nitrobenzene (HC Orange No. 3), 1-amino-5-chloro-4-[(2,3-dihydroxypropyl)amino]-2-nitrobenzene (HC Red No. 10), 5-chloro-1,4-[di(2,3-dihydroxypropyl)amino]-2-nitrobenzene (HC Red No. 11), 2-[(2-hydroxyethyl)amino]-4,6-dinitrophenol, 4-ethylamino-3-nitrobenzoic acid, 2-[4 (4-amino-2-nitrophenyl)amino]benzoic acid, 2-chloro-6-ethylamino-4-nitrophenol, 2-amino-6-chloro-4-nitrophenol, 4-[(3-hydroxypropyl)amino]-3-nitrophenol, 2,5-diamino-6-nitropyridine, 1,2,3,4-tetrahydro-6-nitroquinoxaline, 7-amino-3,4-dihydro-6-nitro-2H-1,4-benzoxazine (HC Red No. 14), 1-amino-2-[(2-hydroxyethyl)amino]-5-nitrobenzene (HC Yellow No. 5), 1-(2-hydroxyethoxy)-2-[(2-hydroxyethyl)amino]-5-nitrobenzene (HC Yellow No. 4), 1-[(2-hydroxyethyl)amino]-2-nitrobenzene (HC Yellow No. 2), 2-[(2-hydroxyethyl)amino]-1-methoxy-5-nitrobenzene, 2-amino-3-nitrophenol, 1-(2-hydroxyethoxy)-3-methylamino-4-nitrobenzene, 2,3-(dihydroxypropoxy)-3-methylamino-4-nitrobenzene, 2-[(2-hydroxyethyl)amino]-5-nitrophenol (HC Yellow No. 11), 3-[(2-aminoethyl) amino]-1-methoxy-4-nitrobenzene hydrochloride (HC Yellow No. 9), 1-[(2-ureidoethyl)amino]-4-nitrobenzene, 4,-[(2,3-dihydroxypropyl)amino]-3-nitro-1-trifluoromethylbenzene (HC Yellow No. 6), 1-chloro-2,4-bis [(2-hydroxyethyl)amino]-5-nitrobenzene (HC Yellow No. 10), 4-[(2-hydroxyethyl)amino]-3-nitro-1-methylbenzene, 1-chloro-4-[(2-hydroxyethyl)amino]-3-nitrobenzene (HC Yellow No. 12), 4-[(2-hydroxyethyl)amino]-3-nitro-1-trifluoromethylbenzene (HC Yellow No. 13), 4-[(2-hydroxyethyl)amino]-3-nitrobenzonitrile (HC Yellow No. 14), 4-[(2-hydroxyethyl)amino]-3-nitrobenzamide (HC Yellow No. 15), 1,4-di[2,3-dihydroxypropyl)amino]-9,10-anthraquinone, 1-[(2-hydroxyethyl)amino]-4-methylamino-9,10-anthraquinone (CI 61505, Disperse Blue No. 3), 2-[(2-aminoethyl)amino]-9,10-anthraquinone (HC Orange No. 5), 1-hydroxy-4-[(4-methyl-2-sulfophenyl)amino]-9,10-anthraquinone, 1-[(3-aminopropyl)amino]-4-methylamino-9,10-anthraquinone (HC Blue No. 8), 1-[(3-aminopropylamino)-9,10-anthraquinone (HC Red No. 8), 1,4-diamino-2-methoxy-9,10-anthraquinone (CI 62015, Disperse Red No. 11, Solvent Violet No. 26), 1,4-dihydroxy-5,8-bis[(2-hydroxyethyl)amino]-9,10-anthraquinone (CI 62500, Disperse Blue No. 7, Solvent Blue No. 69), 9-(dimethylamino)benzo[a]phenoxazin-7-ium chloride (CI 51175; Basic Blue No. 6), di[4-(diethylamino)phenyl]-[4-(ethylamino)naphthyl]carbenium chloride (CI 42595; Basic Blue No. 7), 3,7-di-(dimethylaminophenothiazin-5-ium chloride (CI 52015; Basic Blue No. 9), di[4-(dimethylamino)phenyl]-[4-(phenylamino)naphthyl] carbenium chloride (CI 44045; Basic Blue No. 26), 2[(4-(ethyl(2-hydroxyethyl)amino)phenyl)azo]-6-methoxy-3-methylbenzothiazolium methyl sulfate (CI 11154; Basic Blue No. 41), 1-8-amino-2-bromo-5-hydroxy-4-imino-6-[(3-(trimethylammonio)phenyl)amino]-1(4H)-napthalenone chloride (CI 56059; Basic Blue No. 99), bis[4-(dimethylamino)phenyl][4-(methylamino)phenyl] carbenium chloride (CI 42535; Basic Violet No. 1), tris-[4-(dimethylamino)phenyl]carbenium chloride (CI 42555; Basic Violet No. 3), 2-[3,6-(diethylamino) dibenzopyranium-9-yl]benzoic acid chloride (CI 45170; Basic Violet No. 10), di(4-aminophenyl)(4-amino-3-methylphenyl)carbenium chloride (CI 42510; Basic Violet No. 14), 1,3-bis[(2,4-diamino-5-methylphenyl)azo]-3-methylbenzene (CI 21010; Basic Brown No. 4), 1-[(4-aminophenyl)azo]-7-(trimethylammonio)-2-naphthol chloride (CI 12250; Basic Brown No. 16), 1-[(4-amino-2- nitrophenyl)azo]-7-(trimethylammonio)-2-naphthol chloride (Basic Brown No. 17), 1-[(4-amino-2-nitrophenyl) azo]-7-(trimethylammonio)-2-naphthol chloride (CI 12251; Basic Brown No. 17), 3,7-diamino-2,8-dimethyl-5-phenylphenazinium chloride (CI 50240; Basic Red No. 2), 1,4-dimethyl-5-[(4-(dimethylamino)phenyl)azo]-1,2,4-triazolium chloride (CI 11055; Basic Red No. 22), 2-hydroxy-1-[(2-methyoxyphenyl)azo]-7-(trimethylammonio)-naphthalene chloride (CI 12245; Basic Red No. 76), 2-[2-((2,4-dimethyoxyphenyl)amino)ethenyl]-1,3,3-trimethyl-3H-indol-1-ium chloride (CI 48055; Basic Yellow No. 11), 3-methyl-1-phenyl-r-[(3-(trimethylammonio)phenyl)azo]-pyrozol-5-one chloride (CI 12719; Basic Yellow No. 57), bis[4-(diethylamino) phenyl)phenylcarbenium hydrogen sulfate (1:1) (CI 42040; Basic Green No. 1), 1-[di(2-hydroxyethyl)amino]-3-methyl-4-[(4-nitrophenyl)azo]benzene (CI 11210, Disperse Red No. 17), 4-[(4-aminophenyl)azo]-1-[di(2-hydroxyethyl)amino]-3-methylbenzene (HC Yellow No. 7), 2,6-diamino-3-[pyridin-3-yl)azo]pyridine, 6-hydroxy-5-[(4-sulfophenyl (azo]-2-naphthalene sulfonic acid disodium salt (CI 15985; Food Yellow No. 3; FD&C Yellow No. 6), 2,4-dinitro-1-naphthol-7-sulfonic acid disodium salt (CI 10316; Acid Yellow No. 1; Food Yellow No. 1), 1-(indane-1,3-dion-2-yl)quinolone-x,x-sulfonic acid (mixture of mono- and disulfonic acid), (CI 47005; D&C Yellow No. 10; Food Yellow No. 13; Acid Yellow No. 3), 5-hydroxy-1-(4-sulfophenyl)-4-[(4-sulfophenyl)azo]pyrazole-3-carboxylic acid trisodium salt (CI 19140; Food Yellow No. 4; Acid Yellow No. 23), 9-(2-carboxyphenyl)-6-hydroxy-3H-xanthen-3-one (CI 45350; Acid Yellow No. 73; D&C Yellow No. 8), 5-[(2,4-dinitrophenyl)amino]-2-phenylaminobenzenesulfonic acid sodium salt (CI 10385; Acid Orange No. 3), 4-[2,4-dihydroxyphenyl)azo]benzenesulfonic acid sodium salt (CI 14270; Acid Orange No. 6), 4-[(2-hydroxynaphth-1-yl(azo] benzenesulfonic acid sodium salt (CI 15510; Acid Orange No. 7), 4-[(2,4-dihydroxy-3-[(2,4-dimethylphenyl)azo] phenyl)azo]benzene sulfonic acid sodium salt (CI 20170; Acid Orange No. 24), 4-hydroxy-3-[(4-sulfonaphth-1-yl) azo]-1-naphthalenesulfonic acid disodium salt (CI 14720; Acid Red No. 14), 6-hydroxy-5-[(4-sulfonaphth-1-yl)azo]-2,4-naphthalenedisulfonic acid trisodium salt (CI 16255; Ponceau 4R; Acid Red No. 18), 3-hydroxy-4-[(4-sulfonaphth-1-yl)azo]-2,7-naphthalenedisulfonic acid trisodium salt (CI 16185; Acid Red No. 27), 8-amino-1-hydroxy-2-(phenylazo)-3,6-naphthalenedisulfonic acid disodium salt (CI 17200; Acid Red No. 33), 5-(acetylamino)-4-hydroxy-3-[(2-methylphenyl)azo]-2,7-naphthalenedisulfonic acid disodium salt (CI 18065; Acid Red No. 35), 2-(3-hydroxy-2,4,5,7-tetraiododibenzopyran-6-on-9-yl)benzoic acid disodium salt (CI 45430; Acid Red No. 51), N-[6-(diethylamino)-9-(2,4-disulfophenyl)-3H-xanthen-3-ylidene]-N-ethylethaneammonium hydroxide, internal salt, sodium salt (CI 45100; Acid Red No. 52), 8-[(4-(phenylazo) phenyl)azo]-7-naphthol-1,3-disulfonic acid disodium salt (CI 27290; Acid Red No. 73), 2',4',5',7'-tetrabromo-3',6'-dihydroxyspiro[isobenzofurane-1(3H),9'[9H]-xanthen]-3-one disodium salt (CI 45380; Acid Red No. 87), 2',4',5',7'-tetrabromo-4,5,6,7-tetrachloro-3',6'-dihydroxyspiro[isobenzofurane-1(3H),9'[9H]-xanthen]-3-one disodium salt (CI 45410; Acid Red No. 92), 3',6'-dihydroxy-4'5'-diiodospiro[isobenzofurane-1(3H),9'(9H)-xanthen]-3-one disodium salt (CI 45425; Acid Red No. 95), (2-sulfophenyl) di[4-(ethyl((4-sulfophenyl)methyl)amino)phenyl] carbenium disodium salt, betaine (CI 42090; Acid Blue No. 9; FD&C Blue No. 1), 1,4-bis[(2-sulfo-4-methylphenyl) amino]-9,10-anthraquinone disodium salt (CI 61570; Acid Green No. 25), bis[4-(dimethylamino)phenyl]-(3,7-disulfo-2-hydroxynaphth-1-yl)carbenium internal salt, monosodium salt (CI 44090; Food Green No. 4; Acid Green No. 50), bis[4-diethylamino)phenyl](2,4-disulfophenyl)carbenium internal salt, sodium salt (2:1) (CI 42045; Food Blue No. 3; Acid Blue No. 1), bis[4-diethylamino)phenyl](5-hydroxy-2,4-disulfophenyl)carbenium internal salt, sodium salt (2:1) (CI 42051; Acid Blue No. 3), 1-amino-4-(cyclohexylamino)-9,10-anthraquinone-2-sulfonic acid sodium salt (CI 62045; Acid Blue No. 62), 2-(1,3-dihydro-3-oxo-5-sulfo-2H-indol-2-ylidene)-2,3-dihydro-3-oxo-1H-indole-5-sulfonic acid disodium salt (CI 73015, Acid Blue No. 74), 9-(2-carboxyphenyl)-3-[(2-methylphenyl)amino]-6-[(2-methyl-4-sulfophenyl)amino]xanthylium internal salt, monosodium salt (CI 45190; Acid Violet No. 9), 1-hydroxy-4-[(4-methyl-2-sulfophenyl)amino]-9,10-anthraquinone sodium salt (CI 60730; D&C Violet No. 2; Acid Violet No. 43), bis[3-nitro-4-[(4-phenylamino)-3-sulfophenylamino] phenyl]sulfone (CI 10410; Acid Brown No. 13), 5-amino-4-hydroxy-6-[(4-nitrophenyl)azo]-3-(phenylazo)-2,7-naphthalene disulfonic acid disodium salt (CI 20470; Acid Black No. 1), 3-hydroxy-4-[(2-hydroxynaphth-1-yl)azo]-7-nitro-1-naphthalenesulfonic acid chromium complex (3:2) (CI 15711; Acid Black No. 52), 3-[(2,4-dimethyl-5-sulfophenyl)azo]-4-hydroxy-1-naphthalenesulfonic acid disodium salt (CI 14700; Food Red No. 1; Ponceau SX; FD&C Red No. 4), 4-(acetylamino)-5-hydroxy-6-[(7-sulfo-4-[(4-sulfophenyl]azo]naphth-1-yl)azo]-1,7-naphthalene disulfonic acid tetrasodium salt (CI 28440, Food Black No. 1), and 3-hydroxy-4-(3-methyl-5-oxo-1-phenyl-4,5-dihydro-1H-pyrazol-4-ylazo)naphthalene-1-sulfonic acid sodium salt, chromium complex (Acid Red No. 195), in particular 2,6-diamino-3-(pyridin-3-yl)azopyridine, 8-amino-2-bromo-5-hydroxy-4-imino-6-[(3-(trimethylammonio)phenyl)amino]-1(4H)-naphthalenone chloride (CI 56059; Basic Blue No. 99), or nitro dyes, such as 1,4-bis[(2-hydroxyethyl)amino]-2-nitrobenzene, 1-(2-hydroxyethyl)amino-2-nitro-4-[di((2-hydroxyethyl)amino] benzene (HC Blue No. 2), 1-amino-3-methyl-4-[(2-hydroxyethyl)amino]-6-nitrobenzene (HC Violet No. 1), 4-[ethyl-(2-hydroxyethyl)amino]-1-[(2-hydroxyethyl) amino]-2-nitrobenzene hydrochloride (HC Blue No. 12), 4-[di(2-hydroxyethyl)amino]-1-[((2-hydroxymethyl) amino]-2-nitrobenzene (HC Blue No. 11), 1-[2,3-dihydroxypropyl)amino]-4-[methyl-(2-hydroxyethyl) amino]-2-nitrobenzene (HC Blue No. 10), 1-[(2,3-dihydroxypropyl)amino]-4-[ethyl-(2-hydroxyethyl)amino]-2-nitrobenzene hydrochloride (HC Blue No. 9), 1-(3-hydroxypropylamino)-4-[di-(2-hydroxyethyl)amino]-2-nitrobenzene (HC Violet No. 2), 1-methylamino-4-[methyl (2,3-dihydroxypropyl)amino-2-nitrobenzene (HC Blue No. 6), 2-((4-amino-2-nitrophenyl)amino)-5-dimethylaminobenzoic acid (HC Blue No. 13), 1-amino-4-[(2-hydroxyethyl)amino]-2-nitrobenzene (HC Red No. 7), 2-amino-4,6-dinitrophenol, 4-amino-2-nitrodiphenylamine (HC Red No. 1), 1-amino-4-[di-(2-hydroxyethyl)amino]-2-nitrobenzene hydrochloride (HC Red No. 13), 1-amino-5-chloro-4-[(2-hydroxyethyl)amino]-2-nitrobenzene, 4-amino-1-[(2-hydroxyethyl)amino]-n-nitrobenzene (HC Red No. 3), 4-amino-3-nitrophenol, 4-[(2-hydroxyethyl) amino]-3-nitrophenol, 1-[(2-aminoethyl)amino]-4-(2-hydroxyethyl)amino]-2-nitrobenzene (HC Orange No. 2), 4-(2,3-dihydroxypropoxy)-1-[(2-hydroxyethyl)amino]-2-nitrobenzene (HC Orange No. 3), 1-amino-5-chloro-4-[(2,3-dihydroxypropyl)amino]-2-nitrobenzene (HC Red No. 10), 5-chloro-1,4-[di(2,3-dihydroxypropyl)amino]-2-nitrobenzene (HC Red No. 11), 2-[(2-hydroxyethyl)amino]-

4,6-dinitrophenol, 4-ethylamino-3-nitrobenzoic acid, 2-[4 (4-amino-2-nitrophenyl)amino]benzoic acid, 2-chloro-6-ethylamino-4-nitrophenol, 2-amino-6-chloro-4-nitrophenol, 4-[(3-hydroxypropyl)amino]-3-nitrophenol, 2,5-diamino-6-nitropyridine, 1,2,3,4-tetrahydro-6-nitroquinoxaline, 7-amino-3,4-dihydro-6-nitro-2H-1,4-benzoxazine (HC Red No. 14), 1-amino-2-[(2-hydroxyethyl)amino]-5-nitrobenzene (HC Yellow No. 5), 1-(2-hydroxyethoxy)-2-[(2-hydroxyethyl)amino]-5-nitrobenzene (HC Yellow No. 4), 1-[(2-hydroxyethyl)amino]-2-nitrobenzene (HC Yellow No. 2), 2-[(2-hydroxyethyl)amino]-1-methoxy-5-nitrobenzene, 2-amino-3-nitrophenol, 1-(2-hydroxyethoxy)-3-methylamino-4-nitrobenzene, 2,3-(dihydroxypropoxy)-3-methylamino-4-nitrobenzene, 2-[(2-hydroxyethyl)amino]-5-nitrophenol (HC Yellow No. 11), 3-[(2-aminoethyl) amino]- 1-methoxy-4-nitrobenzene hydrochloride (HC Yellow No. 9), 1-[(2-ureidoethyl)amino]-4-nitrobenzene, 4,-[(2,3-dihydroxypropyl)amino]-3-nitro-1-trifluoromethylbenzene (HC Yellow No. 6), 1-chloro-2,4-bis [(2-hydroxyethyl)amino]-5-nitrobenzene (HC Yellow No. 10), 4-[(2-hydroxyethyl)amino]-3-nitro-1-methylbenzene, 1-chloro-4-[(2-hydroxyethyl)amino]-3-nitrobenzene (HC Yellow No. 12), 4-[(2-hydroxyethyl)amino]-3-nitro-1-trifluoromethylbenzene (HC Yellow No. 13), 4-[(2-hydroxyethyl)amino]-3-nitrobenzonitrile (HC Yellow No. 14), and 4-[(2-hydroxyethyl)amino]-3-nitrobenzamide (HC Yellow No. 15). Especially preferred direct dyes here are 4-amino-1-[(2-hydroxyethyl)amino]-n-nitrobenzene (HC Red No. 3), 1-amino-4-[di-(2-hydroxyethyl)amino]-2-nitrobenzene hydrochloride (HC Red No. 13), 8-amino-2-bromo-5-hydroxy-4-imino-6-[(3-(trimethylammonio) phenyl)amino]-1(4H)-napthalenone chloride (CI 56059; Basic Blue No. 99), 4-[ethyl-(2-hydroxyethyl)amino]-1-[(2-hydroxyethyl)amino]-2-nitrobenzene hydrochloride (HC Blue No. 12), 1-(2-hydroxyethyl)amino-2-nitro-4-[di(2-hydroxyethyl)amino]benzene, 4-[ethyl-(2-hydroxyethyl) amino]-1-[((2-hydroxyethyl)amino]-t-nitrobenzene hydrochloride, 4-amino-3-nitrophenol, 1-amino-4-[di(2-hydroxyethyl)amino]-2-nitrobenzene hydrochloride, and/or 2-amino-6-chloro-4-nitrophenol, as well as 2,6-diamino-3-(pyridin-3-yl)azopyridine.

The direct dyes may be used in this chromophore composition in a quantity of approximately 0.01 to 10 weight %, and preferably 0.1 to 5 weight %.

In the multicomponent kit, the oxidant is also present separately from the chromophore composition. The quantity of hydrogen peroxide, or hydrogen peroxide products of addition, or oxidative-action enzymes contained in the multicomponent kit is dimensioned such that it suffices to convert the mixing of the color precursors quantitatively into the oxidant dye. The oxidant may be present either in a form ready for use or as a dry substance that can be employed after the addition of a suitable solvent.

As a rule, hydrogen peroxide or its compounds of addition to urea, melamine or sodium bromate are used as the oxidant that is also contained in the multicomponent kit of the invention, and hydrogen peroxide is especially preferred. In general, hydrogen peroxide or the products of addition of hydrogen peroxide for oxidizing the color precursors are used in a concentration of from 1 to 12 weight percent.

However, the enzymatic oxidation of the color precursors with the aid of air or oxygen is gentler to the hair. It is distinguished by especially mild conditions. The pH value is in the slightly acidic to slightly alkaline range, and the enzyme proteins employed do not attack the hair structure. In contrast to the use of peroxides, however, "lightening" of the hair is not possible if oxidatively acting enzymes are used.

For oxidatively creating oxidation colors with the aid of air or oxygen in the presence of enzymes, single-stage or multistage enzymatic oxidation systems are available. In the single-stage enzyme systems, aromatic phenols and amines in a dye mixture can be oxidized directly into the polymeric dye by supplying oxygen, without adding peroxides. Phenol oxidases, preferably laccases, are suitable for this. In contrast, in the multistage enzymatic oxidation systems, a plurality of enzymes are required for producing the dye.

For a multistage, enzymatic oxidation system for producing the oxidant dye from the color precursors, a combination of an oxygen-oxidoreductase and substrate system with a peroxidase can be employed. Examples of an oxygen-oxidoreductase and substrate system are the following:

Glucose oxidase (EC1.1.3.4)/D-glucose
Alcohol oxidase (EC1.1.3.13)/ethanol
Pyruvate oxidase (EC1.2.3.3)/pyruvate
Oxalate oxidase (EC1.2.3.4)/oxalate
Cholesterol oxidase (EC1.1.3.6)/cholesterol
Uricase (EC1.7.3.3)/uric acid
Lactate oxidase/lactic acid
Xanthine oxidase (EC1.1.3.22)/xanthine.

The classifications for the enzymes as given in parentheses are in accordance with the Classification of the International Union of Biochemistry on Nomenclature and Classification of Enzymes (1984).

The form of preparation for the chromophore composition and also for the oxidative colorant for hair that is ready to use may for example be a solution, and in particular an aqueous or aqueous-alcohol solution. The particularly preferred forms of preparation, however, are a cream, gel, or emulsion. Their composition represents a mixture of the dye components with the additives typical for such preparations.

The compositions contained in the multicomponent kit according to the invention for creating a nonoxidative dye (component (I)) contain as colorants the above-named direct dyes, and these colorants are used in a total quantity of approximately 0.01 to 10 weight %, preferably 0.1 to 5 weight %.

The nonoxidative dye can for instance be in the form of a solution, in particular an aqueous or aqueous-alcohol solution. The especially preferred preparation forms, however, are a cream, gel, aerosol foam or emulsion. Their composition is a mixture of the dye components with the usual additives for such preparations.

Conventional additives in solutions, creams, emulsions, or gels or aerosol foams used in oxidative or nonoxidative dyes, are for example solubilizers with water, low aliphatic alcohols, such as ethanol, n-propanol and isopropanol, or glycols, such as glycerin and 1,2-propylene glycol, and also neutralizers or emulsifiers selected from the anionic, cationic, amphoteric or nonionic classes of surfactants, such as fatty alcohol sulfates, ethoxylated fatty alcohol sulfates, alkyl sulfonates, alkyl benzene sulfonates, alkyltrimethylammonium salts, alkyl betaines, ethoxylated fatty alcohols, ethoxylated nonylphenols, fatty acid alkanolamides, ethoxylated fatty alcohols, ethoxylated nonylphenols, fatty acid alkanolamides, ethoxylated fatty acid esters; also thickeners such as higher fatty alcohols, starch or cellulose derivatives, perfumes, hair pretreatment agents, conditioners, hair volumizers, preservatives; and vaseline, paraffin oil and fatty acids, as well as conditioners such as cationic resins, lanolin derivatives, cholesterol, pantothenic acid and betaine. The aforementioned ingredients are used in the customary quantities for such purposes, for example the neutralizers and emulsifiers in a concentration of approximately 0.5 to 30 weight-percent (referred to the chromophore composition), the thickeners in a quantity of approximately 0.1 to 25 weight-percent (referred to the chromophore composition) and the conditioners in a concentration of approximately 0.1 to 5.0 weight-percent (referred to the chromophore composition).

The pH value of the oxidative or nonoxidative dye ready for use is as a rule 3 to 11, and preferably 5 to 9.

In the mixing of the preferably alkaline chromophore composition, the pH value of the ready-to-use hair dye according to the invention is adjusted by means of the usually acidic oxidant to a pH value that is varied by means of the quantities of alkali in the chromophore composition and of acid in the oxidant, and by the mixture ratio.

To adjust the pH value suitable for the dyeing, alkylamines, alkali hydroxides, or ammonium hydroxide, and alkali carbonates or ammonium carbonates, preferably ammonium hydroxide, or such acids as lactic acid, acetic acid, tartaric acid, phosphoric acid, hydrochloric acid, citric acid, ascorbic acid and boric acid.

Particularly in the enzymatically catalyzed oxidation, the use of a buffer system is recommended to control the pH value. Citrate buffers, phosphate buffers or borate buffers can be used. The use of a borate buffer (boric acid/NaOH) or a phosphate buffer ($KH_2PO_4/K_2HPO_4$) is preferred.

In the case of oxidative dyeing or coloring, immediately prior to use one of the aforementioned oxidants is mixed with the chromophore composition which contains the colorant precursors and optionally direct dyes as well as the other adjuvants, and is applied to the hair. Depending on the desired color intensity, the mixture is left to act for 5 to 60 minutes (preferably 15 to 30 minutes), at a temperature of 20 to 50° C. and in particular 30 to 40° C. The hair is then rinsed with water and optionally washed with a shampoo.

The chromophore composition and the oxidant are mixed with one another in a mixture ratio by weight of 5:1 to 1:3, and a ratio by weight of 1:1 to 1:2 is especially preferred.

In the case of the nonoxidative dyeing or coloring, the dye is applied to the hair. Depending on the desired color intensity, this mixture is then left to act for 5 to 60 minutes (preferably 15 to 30 minutes), at a temperature of 20 to 50° C. and in particular 30 to 40° C. The hair is then rinsed with water and optionally washed with a shampoo.

Another essential ingredient of the multicomponent kit of the invention is the composition, or component (II), for stripping the fibers dyed with oxidative dyes and/or direct dyes, which composition contains a combination of reductones and/or thiols and/or sulfites.

Examples of reductones that can be used are ascorbic acid or isoascorbic acid or their salts or esters, such as 6-O-palmitoyl ascorbate, hydroxypropanediol (triose reductone), 2,3-dihydroxy-2-cyclopenten-1-one (reductic acid) or mixtures of these compounds, preferably in a quantity of from 1 to 50 weight % and in particular 2 to 10 weight %, the use of ascorbic acid or isoascorbic acid and in particular ascorbic acid being preferred. When ascorbic acid acids or isoascorbic acid acids are used, the free acid can also be created in situ from the salts, for instance the alkali metal ascorbates or alkaline earth metal ascorbates, or the alkali metal isoascorbates or alkaline earth metal ascorbates, respectively, by adding an acid. This is especially advantageous at higher concentrations because of the better solubility of the salts in water. Examples of ascorbic acid salts or isoascorbic acid salts that can be considered are particularly the calcium salt, the magnesium salt or the sodium salt of ascorbic acid or isoascorbic acid.

As the thiols, cysteine or its salts, N-acetyl cysteine, cysteamine or its salts, mercaptoacetaldehyde, penicillamine, glutathione, homocysteine or its salts, and/or calcium thioglycolate can be used, with cysteine and its salts being especially preferred.

The stripper can also contain sulfites, such as alkali sulfites or alkaline earth sulfites and in particular sodium sulfite, to prevent reoxidation of any colorant precursors that may remain in the hair.

The quantity of thiol used is from 0.1 to 10 weight %, preferably 2 to 5 weight %, while the sulfite is used in a quantity of 0.001 to 5 weight % and preferably in a quantity of from 0.01 to 0.5 weight %.

In an especially preferred embodiment, the stripper contains a combination of at least one reductone, preferably ascorbic acid, at least one thiol, preferably cysteine and/or cysteine hydrochloride, and at least one sulfite, preferably sulfite.

However, it is also possible for the color removal to use a stripper that contains a thiol and/or a sulfite, or a reductone in combination with a thiol or a sulfite.

The composition for reductive removal of color from the fibers colored with a combination of oxidative dyes and/or direct dyes (hereinafter called a "stripper") can be in the form of an aqueous-alcohol solution, in particular a water and n-propanol solution, or in the form of a gel, cream, emulsion or foam; the stripper may be packaged in the form of either a single-component preparation or a multicomponent preparation. In addition to powdered form, the stripper may also be packaged as a tablet—including an effervescent tablet—or granulate to guard against dust development. From this the stripper is then prepared before use, using cold or warm water and optionally with the addition of one or more of the adjuvants named below. However, it is also possible for these adjuvants (if they are in solid form) already to be contained in the stripper power or stripper granulate or effervescent tablet. Dust development can be additionally reduced by wetting the powder with oil or wax.

The stripper may contain additional adjuvants, such as solvents water, low aliphatic alcohols, such as ethanol, n-propanol and isopropanol, or glycols, such as glycerin and 1,2-propylene glycol, and also neutralizers or emulsifiers selected from the anionic, cationic, amphoteric or nonionic classes of surfactants, such as fatty alcohol sulfates, ethoxylated fatty alcohol sulfates, alkyl sulfonates, alkyl benzene sulfonates, alkyltrimethylammonium salts, alkyl betaines, ethoxylated fatty alcohols, ethoxylated nonylphenols, fatty acid alkanolamides, ethoxylated fatty alcohols, ethoxylated nonylphenols, fatty acid alkanolamides, ethoxylated fatty acid esters; also thickeners such as higher fatty alcohols, starch or cellulose derivatives, perfumes, hair pretreatment agents, conditioners, hair volumizers, preservatives, vaseline, paraffin oil and fatty acids, as well as conditioners such as cationic resins, lanolin derivatives, cholesterol, pantothenic acid and betaine.

The pH value of the stripper is approximately 1.8 to 6 and in particular 2.5 to 4. If needed, the desired pH value can be adjusted by adding additional acids, such as α-hydroxycarboxylic acids such as lactic acid, tartaric acid, citric acid or maleic acid, phosphoric acid, acetic acid, glycolic acid, salicylic acid, glutathione, or gluconic acid lactone, or such alkalizing agents as alkanolamines, alkylamines, alkali hydroxides, ammonium hydroxides, alkali carbonates, ammonium carbonates, or alkali phosphates.

The action time of the stripper, depending on the color to be removed and on the temperature (approximately 20 to 50° C.) is from 5 to 60 minutes and in particular 15 to 30 minutes; the stripping process can be speeded up by adding heat. Once the stripper action time is ended, the hair is rinsed with water, optionally washed with a shampoo and a rinse, preferably an acidic rinse, treated, and then dried.

Naturally, the use of the stripper according to the invention of component (II) is not limited to removing color from the hair dyes created with component (I) of the multicomponent kit of the invention. On the contrary, the stripper preparation of component (II) can be used very generally to remove color from colored hair, even if the colors have not been created with the aid of the dye of component (I) according to the invention but instead in some completely different and independent way. Furthermore, the stripper preparation of component (II) according to the invention is also suited for removing color from other natural or synthetic fibers, such as cotton, wool, silk, viscose, nylon, and cellulose acetate, if they have been dyes with oxidative dyes and/or direct dyes, and is not limited to removing color from keratin fibers such as human hair.

The subject of the present invention is therefore also the use of a combination of reductones, such as ascorbic acid or isoascorbic acid or their salts or esters, such as 6-O-palmitoyl ascorbate, hydroxypropanediol (triose reductone), 2,3-dihydroxy-2-cyclopenten-1-one (reductic acid) or mixtures of these compounds, in particular ascorbic acid, and/or thiols, in particular cysteine or its salts, and/or sulfites, in particular sodium sulfite, for the reductive stripping of fibers, in particular hair, dyed with oxidative dyes and/or direct dyes, as well as the above-described stripping composition. The use of a combination of at least one reductone, in particular ascorbic acid or isoascorbic acid or its salts, and at least one thiol, in particular cysteine and/or cysteine hydrochloride, and at least one sulfite, in particular sodium sulfite, is especially preferred.

The stripping composition according to the invention enables fast, gentle, and uniform removal of color from fibers dyed with oxidative dyes and/or direct dyes without residual discoloration of the hair.

The following examples are intended to explain the subject in further detail without limiting it to these examples.

EXAMPLES

Examples 1.1–1.5
a. Oxidative Hair Dyes

| | |
|---|---|
| Developer substance(s) (optionally mixed NH$_3$ (25% aqueous solution) or NaOH (10% aqueous solution)) | Quantities with as given in Table 1 |
| Coupler substance(s) (optionally mixed NH$_3$ (25% aqueous solution) or NaOH (10% aqueous solution)) | Quantities with as given in Table 1 |
| Nitro dyes | Quantities as given in Table 1 |
| Disodium ethylene diaminotetraacetate | 0.30 g |
| Sodium sulfite | 0.40 g |
| Sodium lauryl ether sulfate (28% aqueous solution) | 10.00 g |
| Isopropanol | 10.00 g |
| Ammonia (25% aqueous solution) | 9.10 g |
| Water, fully deionized to make up | 100.00 g |

5 g of the above chromophore composition are mixed with 5 g of a 6% hydrogen peroxide solution. The oxidative hair dye ready for use that is obtained is applied to the hair and distributed evenly using an artist's brush. After an action time of 30 minutes at 40° C., the hair is rinsed with lukewarm water and then dried.

| | |
|---|---|
| b1. Stripper gel: | |
| Ascorbic acid | 5.00 g |
| Methyl hydroxy ethyl cellulose (Tylose MHB 10.000P made by Hoechst, Germany) | 2.00 g |
| Cysteine | 2.00 g |
| Sodium sulfite | 0.05 g |
| Water to make up | 100.00 g |
| b2. Stripper gel: | |
| Isoascorbic acid | 5.00 g |
| Methyl hydroxy ethyl cellulose (Tylose MHB 10.000P made by Hoechst, Germany) | 2.00 g |
| Cysteine | 2.00 g |
| Sodium sulfite | 0.05 g |
| Water to make up | 100.00 g |
| b3. Stripper gel: | |
| Sodium ascorbate | 5.60 g |
| Methyl hydroxy ethyl cellulose (Tylose MHB 10.000P made by Hoechst, Germany) | 1.50 g |
| Cysteine hydrochloride | 2.50 g |
| Sodium sulfite | 0.05 g |
| Citric acid | 5.00 g |
| Water to make up | 100.00 g |
| b4. Stripper gel: | |
| Ascorbic acid | 10.00 g |
| Hydroxy ethyl cellulose | 2.00 g |
| Glutathione | 1.00 g |
| Water to make up | 100.00 g |
| b5. Stripper balsam: | |
| Cetylstearyl alcohol | 4.50 g |
| Cetyl acetate | 0.50 g |
| Dimethicone | 0.50 g |
| Cetyltrimethylammonium chloride | 0.65 g |
| Ascorbic acid | 6.00 g |
| Water, fully deionized, to make up | 100.00 g |
| b6. Stripper gel: | |
| Ascorbic acid | 6.00 g |
| Hydroxy ethyl cellulose | 2.00 g |
| Water to make up | 100.00 g |

The pH value of the stripper gel is adjusted as needed to 2.5 to 3, using a suitable acid or base.

To the dyed hair, the above-described stripper gel is applied and left to act under a plastic hood for 30 minutes at 37° C. (for strippers b1 through b3), 60 minutes at 40° C. (for strippers b4 and b5), and 20 to 60 minutes at 25 to 30° C. (stripper b6), and then the hair is washed thoroughly with water and a shampoo, treated with an acidic conditioning rinse (pH=2 to 3), rinsed with water, and then dried.

The result of this stripping treatment is summarized in Table 1.

TABLE 1

Coloring and color removal results

| No. | Developer/coupler combination plus nitro dye(s) | Tint after dyeing | Color measurement values L, a, b | | | Percentage of color removal |
|---|---|---|---|---|---|---|
| 1.1 | 1,4-Diamino-2-(2-hydroxyethyl) benzene sulfate: 0.62 g<br>1,4-Diamino-2-methylbenzene sulfate: 0.55 g<br>5-Amino-2-methylphenol: 061 g | deep violet | untreated hair:<br>37.29;<br>after coloring:<br>25.24;<br>after stripping a single time with b2:<br>35.95; | +8.13;<br><br>+12.32<br><br>+9.42; | +15.88<br><br>+3.35<br><br>+14.42 | 87 |
| 1.2 | 4-Amino-2-(aminomethyl)phenol hydrochloride: 1.05 g<br>5-Amino-2-methylphenol: 061 g | orange | untreated hair:<br>37.29;<br>after coloring:<br>30.22;<br>after stripping a single time with b1:<br>37.57; | +8.13;<br><br>+14.32;<br><br>+9.35; | +15.88<br><br>+14.00<br><br>+16.71 | 84 |
| 1.3 | 1,4-Diamino-2-methylbenzene sulfate: 0.44 g<br>4-Amino-3-methylphenol: 0.37 g<br><br>2,4-Diamino-1-(2-hydroxyethoxy) benzene dihydrochloride: 0.48 g<br>5-Amino-2-methylphenol: 0.37 g | violet | untreated hair:<br>37.29;<br>after coloring:<br>26.31;<br>after stripping a single time with b3:<br>39.77; | +8.13;<br><br>+4.95<br><br>+9.37; | +15.88<br><br>+3.55<br><br>+17.90 | 79 |
| 1.4 | 4-Amino-3-methylphenol: 0.61 g<br><br>1-Naphthol: 0.36 g<br><br>5-Amino-2methylphenol: 0.31 g<br>4-[Ethyl-(2-hydroxyethyl)amino]-1-[2(2-hydroxyethyl)amino]-2-nitrobenzene hydrochloride (HC Blue No. 12): 0.5 g | violet | untreated hair:<br>37.29;<br>after coloring:<br>30.42;<br><br>after stripping a single time with b1:<br>37.72; | +8.13;<br><br>+10.41;<br><br><br>+9.30; | +15.88<br><br>+7.99<br><br><br>+14.26 | 81 |
| 1.5 | 1,4-Diamino-2-methylbenzene sulfate: 0.22 g<br>4-Amino-3-methylphenol: 0.50 g<br><br>5-Amino-2-methylphenol: 0.61 g | red | untreated hair:<br>83.29;<br>after coloring:<br>47.18;<br>after stripping a single time with b3:<br>80.94; | −0.48;<br><br>+31.48<br><br>+0.33; | +10.40<br><br>+17.32<br><br>+15.74 | 90 |
| 1.6 | 1,4-Diamino-2-methylbenzene sulfate: 0.83 g<br>2-Amino-4-[(2-hydroxyethyl) amino] anisole sulfate: 0.42 g<br>4-Amino-3-methylbenzene: 0.46 g<br>2-Amino-6-chloro-4-nitrophenol: 0.225 g | dark brown | untreated hair:<br>34.41;<br>after coloring:<br>21.22;<br><br>after stripping a single time with b3:<br>33.87; | +7.27<br><br>+4.66;<br><br><br>+7.53; | +13.78<br><br>+3.90<br><br><br>+13.97 | 96 |
| 1.7 | 1,4-Diamino-2-methylbenzene sulfate: 0.83 g<br>2-Amino-4-[(2-hydroxyethyl) amino] anisole sulfate: 0.42 g<br>4-Amino-3-methylphenol: 0.46 g<br>2-Amino-6-chloro-4-nitrophenol: 0.225 g | dark brown | untreated hair:<br>34.41;<br>after coloring:<br>21.22;<br><br>after stripping a single time with b5:<br>33.87; | +7.27<br><br>+4.66;<br><br><br>+7.53; | +13.78<br><br>+3.90<br><br><br>+3.97 | 96 |
| 1.8 | 4-Amino-3-methylphenol: 1.92 g<br><br>1-Naphthol: 0.32 g<br><br>2-Amino-4-[(2-hydroxyethyl) amino] anisole sulfate: 0.61 g<br>5-Amino-2-methylphenol: 1.38 g<br>HC Blue 12: 1.00 g | blue violet | untreated hair:<br>34.41;<br>after coloring:<br>22.82;<br><br>after stripping a single time with b4:<br>35.38; | +7,27;<br><br>+8.86;<br><br><br>+8.95; | +13.78<br><br>+3.87<br><br><br>+12.92 | 86 |
| 1.9 | 4-Amino-3-methylphenol: 1.43 g<br><br>1,4-Diamino-2-methylbenzene sulfate: 0.28 g<br>2-Amino-4-[(2-hydroxyethyl) amino] anisole sulfate: 0.42 g<br>1-Naphthol: 0.21 g<br>5-Amino-2-methylphenol: 0.92 g<br>2-Amino-6-chloro-4-nitrophenol: 0.075 g<br>HC Blue 12: 0.66 g | beaujolais | untreated hair:<br>34.41;<br><br><br>after coloring:<br>22.10;<br><br><br><br>after stripping a single time with b5:<br>32.29; | +7.27<br><br><br><br>+6.80;<br><br><br><br>+8.14; | +13.78<br><br><br><br>+3.54<br><br><br><br>+11.43 | 83 |
| 1.10 | 1,4-Diamino-2-methylbenzene sulfate: 2.2 g<br>5-Amino-2-methylphenol: 1.23 g | deep violet | untreated hair:<br>34.41;<br>after coloring:<br>20.04;<br>after stripping a single time with b6:<br>(60 min., 40° C.) | +7.27;<br><br>+7.55; | +13.78<br><br>+0.08 | 83 |

TABLE 1-continued

Coloring and color removal results

| No. | Developer/coupler combination plus nitro dye(s) | Tint after dyeing | Color measurement values L a b | | | Percentage of color removal |
|---|---|---|---|---|---|---|
| 1.11 | 4,5-Diamino-1-(2-hydroxyethyl)-1H-pyrazole: 1.2 g<br>5-Amino-2-methylphenol: 0.62 g | intensive orangish-red | 31.85; +9.28; +14.54<br>untreated hair:<br>34.41; +7.27; +13.78<br>after coloring:<br>27.66 +23.98; +15.06<br>after stripping a single time with b6:<br>(60 min., 40° C.)<br>33.83; +10.92; +15.08 | | | 78 |
| 1.12 | 1,4-Diamino-2-(2-hydroxyethyl) benzene sulfate: 1.25 g<br>4-(2-Hydroxyethoxy)-1,3-phenylenediamine dihydrochloride: 1.20 g | bluish-black | untreated hair:<br>34.41; +7.27; +13.78<br>after coloring:<br>19.76 +0.70; −2.15<br>after stripping a single time with b6:<br>(60 min., 40° C.)<br>32.21; +10.31; +12.98 | | | 83 |
| 1.13 | 4-Amino-3-methylphenol: 1.92 g<br>1-Naphthol: 0.32 g<br>5-Amino-2-methylphenol: 1.38 g<br>2-Amino-4-[(2-hydroxyethyl)amino]anisole sulfate: 0.61 g | reddish-brown | untreated hair:<br>34.41; +7.27; +13.78<br>after coloring:<br>28.18 +15.19; −11.12<br>after stripping a single time with b6:<br>(60 min., 40° C.)<br>34.65; +9.63; +14.76 | | | 75 |
| 1.14 | 1,4-Diamino-2-methylbenzene sulfate: 0.55 g<br>2-Methyl-1-naphthol acetate: 0.5 g<br>5-Amino-2-methylphenol: 0.31 g | deep violet | untreated hair:<br>34.41; +7.27; +13.78<br>after coloring:<br>20.74; +7.91; −0.53<br>after stripping a single time with b6:<br>(60 min., 40° C.)<br>35.20; +9.05; +14.40 | | | 90 |
| 1.15 | 1,4 Diamino-2-(2-hydroxyethyl) benzene sulfate: 1.2 g<br>5-((2,2,2-Triflouroethyl) amino)-2-methylphenol: 1.0 g | violet | untreated hair:<br>84.20; −1.36; +8.81<br>after coloring:<br>25.22; +18.36; −4.83<br>after stripping a single time with b6:<br>(60 min.,40° C.)<br>70.83; +9.59; +19.81 | | | 69 |
| 1.16 | 1,4-Diamino-2-methylbenzene sulfate: 0.55 g<br>4,5-Diamino-1-(2-hydroxyethyl)-1H-pyrazole: 0.6 g<br>5-Amino-2-methylphenol: 0.62 g | intensive red | untreated hair:<br>34.41; +7.27; +3.78<br>after coloring:<br>21.13; +14.99; +5.29<br>after stripping a single time with b6:<br>(60 min.,40° C.)<br>35.65; +10.35; +16.84 | | | 74 |

Examples 2.1 through 2.30

The coloring is done of bleached hair in the manner described in Example 1 (concentration of the colorant precursors: 0.05 molar).

The stripping is done with the stripping gels b1, b2 or b3.

To the dyed hair, the above-described stripper is applied and left to act under a plastic hood for 30 minutes at 37° C.; and then the hair is washed thoroughly with water and a shampoo, treated with an acidic conditioning rinse (pH=2 to 3), rinsed with water, and then dried.

The result of this stripping treatment is summarized in Table 2.

TABLE 2

Coloring and color removal results

| No. | Developer/coupler combination plus nitro dye(s) | Tint after dyeing | Stripper gel | Duration of stripping (in minutes) | Tint after color removal |
|---|---|---|---|---|---|
| 2.1 | 4-Amino-3-methyl phenol; 2-Amino-4-[(2-hydroxyethyl)amino]anisole sulfate | light violet | b3 | 30 | faintly yellow |
| 2.2 | 1,4-Diamino-2-methylbenzene | dark blue | b3 | 30 | faintly beige |

TABLE 2-continued

Coloring and color removal results

| No. | Developer/coupler combination plus nitro dye(s) | Tint after dyeing | Stripper gel | Duration of stripping (in minutes) | Tint after color removal |
|---|---|---|---|---|---|
| | sulfate; 2-Amino-4-[(2-hydroxyethyl)amino]anisole sulfate | | | | |
| 2.3 | 1,4-Diamino-2-methylbenzene sulfate; 1,3-Dihydroxybenzene | brown | b1 | 30 | beige |
| 2.4 | 1,4-Diamino-2-methylbenzene sulfate; 3-Aminophenol | intensive grayish-violet | b3 | 30 | faintly reddish-brown |
| 2.5 | 1,4-Diamino-2-methylbenzene sulfate; 1-Naphthol | dark blue | b2 | 30 | gray |
| 2.6 | 1,4-Diamino-2-methylbenzene sulfate 3-Amino-6-methoxy-2-(methylamino) pyridine | dark blue | b1 | 30 | brownish |
| 2.7 | 1,4-Diamino-2-methylbenzene sulfate; 5-[(2-Hydroxyethyl)amino]-1,3-benzodioxol hydrochloride | greenish-black | b3 | 30 | greenish |
| 2.8 | 1,4-Diamino-2-methylbenzene sulfate; 1,3-Dihydroxy-2-methylbenzene | brown | b3 | 30 | light brown |
| 2.9 | 4-Amino-3-methylphenol; 5-Amino-2-methylphenol | salmon | b3 | 20 | colorless |
| 2.10 | 4,5-Diamino-1-(2-hydroxyethyl)-1H-pyrazole; 1-Naphthol | intensive fuchsia | b1 | 30 | pink |
| 2.11 | 1,4-Diamino-2-methylbenzene sulfate; 1,3-Di(-2,4-diaminophenoxy)propane | deep blue | b3 | 30 | faint orange-beige |
| 2.12 | 1,4-Diamino-2-(2-hydroxyethyl)benzene sulfate; 5-Amino-2-methylphenol | intensive violet | b2 | 20 | faintly yellowish |
| 2.13 | 4,5-Diamino-1-(2-hydroxyethyl)-1H-pyrazole; 1,3-Dihydroxybenzene | fuschia | b3 | 30 | faint rosé wine color |
| 2.14 | 4,5-Diamino-1-(2-hydroxyethyl)-1H-pyrazole; 3-Aminophenol | red | b3 | 20 | colorless |
| 2.15 | 4,5-Diamino-1-(2-hydroxyethyl)-1H-pyrazole; 3-Amino-6-methoxy-2-methylaminopyridine | blue-black | b3 | 30 | beige-gray |
| 2.16 | 4,5-Diamino-1-(2-hydroxyethyl)-1H-pyrazole; 2-Amino-4-[(2-hydroxyethyl)amino]anisole sulfate | bordeaux-red | b2 | 30 | faint bordeaux-red |
| 2.17 | 4,5-Diamino-1-(2-hydroxyethyl)-1H-pyrazole; 1,3-Dihydroxy-2-methylbenzene | red | b3 | 30 | faint rosé wine color |
| 2.18 | 4-Aminophenol; 5-Amino-2-methylphenol | salmon | b3 | 20 | colorless |
| 2.19 | 1,4-Diaminobenzene; 5-Amino-2-methylphenol | violet | b3 | 30 | faint beige |
| 2.20 | 2,4,5,6-Tetraaminopyrimidine sulfate; 5-Amino-2-methylphenol | blue | b3 | 20 | colorless |
| 2.21 | 2,5-Diamino-4-methylphenol dihydrochloride; 5-Amino-2-methylphenol | deep blue | b3 | 30 | faint gray |
| 2.22 | 4-Amino-3-methylphenol; 2,4-Diamino-6-methylphenol | beige | b3 | 30 | faintly yellowish |
| 2.23 | 1,4-Diamino-2-methylbenzene sulfate; 3-Amino-2-methylphenol | brown | b3 | 30 | light brown |
| 2.24 | 4,5-Diamino-1-(2-hydroxyethyl)-1H-pyrazole; 3-(2-Hydroxyethyl)aminophenol | intensive red | b3 | 30 | faint rosé wine color |
| 2.25 | 4,5-Diamino-1-(2-hydroxyethyl)-1H-pyrazole; 5-(2-Hydroxyethyl) amino-2- | intensive orange | b3 | 30 | faint orange |

TABLE 2-continued

Coloring and color removal results

| No. | Developer/coupler combination plus nitro dye(s) | Tint after dyeing | Stripper gel | Duration of stripping (in minutes) | Tint after color removal |
|---|---|---|---|---|---|
| 2.26 | 4-Amino-3-methylphenol; 5-Amino-2-ethylphenol methylphenol | pinkish-orange | b3 | 20 | colorless |
| 2.27 | 4,5-Diamino-1-(2-hydroxyethyl)-1H-pyrazole; 2-Methyl-1-naphthol acetate | intensive pink | b3 | 30 | faint pink |
| 2.28 | 1,4-Diaminobenzene; 1,3-Diaminobenzene | deep blue | b3 | 30 | beige |
| 2.29 | 1,4-Diamino-2-(2-hydroxyethyl) benzene sulfate; 1,3-Diaminobenzene | deep blue | b3 | 20 | faintly yellowish |
| 2.30 | 4-Amino-3-methylphenol (0.06%); 1-Naphthol (0.04%); 5-Amino-2-methylphenol (0.03 %) | pinkish-red | b2 | 20 | colorless |

Examples 3.1 through 3.32

The coloring is done of bleached hair in the manner described in Example 1 (concentration of the colorant precursors: 0.05 M).

The stripping is done with the stripping gels b1, b2 or b3.

The color removal is done with the following compositions.

A: Stripper Gel (per b6 in Example 1)

B: Stripper solution:

| | |
|---|---|
| Ascorbic acid | 10 g |
| Water, fully deionized | 90 g |
| | 100 g |

C: Stripper balsam:

| | |
|---|---|
| Cetylstearyl alcohol | 4.50 g |
| Cetyl acetate | 0.50 g |
| Dimethicone | 0.50 g |
| Cetyltrimethylammonium chloride | 0.65 g |
| Ascorbic acid | 6.00 g |
| Water, fully deionized, to make up | 100.00 g |

The pH of the stripper balsam is adjusted to 2.5, using a 2% aqueous NaOH solution.

D: Stripper Foam:

| | |
|---|---|
| Cetylstearyl alcohol | 1.30 g |
| PEG-35 castor oil | 0.47 g |
| Cetyltrimethylammonium chloride | 0.94 g |
| Ascorbic acid | 6.00 g |
| Water, fully deionized, to make up | 100.00 g |
| Propane/butane (5 bar) | 6.00 g |

The pH of the stripper foam is adjusted to 2.5, using a 2% aqueous NaOH solution.

The hair is treated for 20 to 60 minutes at 40° C. with the stripper, then washed thoroughly with water and a shampoo and then dried.

The result of this stripping treatment is summarized in Table 3.

TABLE 3

Coloring and color removal results

| No. | Developer/coupler combination plus nitro dye(s) | Tint after dyeing | Stripper gel | Duration of stripping (in minutes) | Tint after color removal |
|---|---|---|---|---|---|
| 3.1 | 4-Amino-3-methylphenol; 2-Amino-4-[(2-hydroxyethyl)amino]anisole sulfate | light violet | B | 60 | faintly yellow |
| 3.2 | 1,4-Diamino-2-methylbenzene sulfate; 2-Amino-4-[(2-hydroxyethyl)amino]anisole sulfate | dark blue | B | 60 | faintly greyish blue |
| 3.3 | 1,4-Diamino-2-methylbenzene sulfate; 1,3-Dihydroxybenzene | brown | C | 45 | light brown |
| 3.4 | 1,4-Diamino-2-methylbenzene sulfate; 3-Aminophenol | intensive grayish-violet | C | 45 | faintly reddish-brown |
| 3.5 | 1,4-Diamino-2-methylbenzene sulfate; 1-Naphthol | dark blue | C | 60 | gray |
| 3.6 | 1,4-Diamino-2-methylbenzene sulfate | dark blue | A | 60 | brown |

TABLE 3-continued

Coloring and color removal results

| No. | Developer/coupler combination plus nitro dye(s) | Tint after dyeing | Stripper gel | Duration of stripping (in minutes) | Tint after color removal |
|---|---|---|---|---|---|
| 3.7 | 3-Amino-6-methoxy-2-(methylamino) pyridine 1,4-Diamin-2-methylbenzene sulfate; 5-[(2-Hydroxyethyl)amino]-1,3-benzodioxol hydrochloride | greenish-black | C | 45 | greenish |
| 3.8 | 1,4-Diamino-2-methylbenzene sulfate; 1,3-Dihydroxy-2-methylbenzene | brown | C | 60 | light brown |
| 3.9 | 4-Amino-3-methylphenol; 5-Amino-2-methylphenol | salmon | D | 20 | colorless |
| 3.10 | 4,5-Diamino-1-(2-hydroxyethyl)-1H-pyrazole; 1-Naphthol | intensive fuchsia | B | 45 | pink |
| 3.11 | 4,5-Diamino-1-(2-hydroxyethyl)-1H-pyrazole; 3,5-Hydroxy-4-methoxybenzoic acid | pinkish-orange | B | 60 | faintly pink |
| 3.12 | 1,4-Diamino-2-(2-hydroxyethyl) benzene sulfate | intensive violet | A | 20 | faintly yellowish |
| 3.13 | 4,5-Diamino-1-(2-hydroxyethyl)-1H-pyrazole; 1,3-Dihydroxybenzene | fuschia | A | 30 | faint rosé wine color |
| 3.14 | 4,5-Diamino-1-(2-hydroxyethyl)-1H-pyrazole; 3-Aminophenol | red | A | 20 | faint beige |
| 3.15 | 4,5-Diamino-1-(2-hydroxyethyl)-1H-pyrazole; 3-Amino-6-methoxy-2-methylaminopyridine | blue-black | B | 60 | gray |
| 3.16 | 4,5-Diamino-1-(2-hydroxyethyl)-1H-pyrazole; 2-Amino-4-[(2-hydroxyethyl)amino]anisole sulfate | bordeaux-red | B | 60 | faint bordeaux-red |
| 3.17 | 4,5-Diamino-1-(2-hydroxyethyl)-1H-pyrazole; 1,3-Dihydroxy-2-methylbenzene | red | B | 60 | faint rosé wine color |
| 3.18 | 4-Aminophenol; 5-Amino-2-methylphenol | salmon | A | 20 | colorless |
| 3.19 | 1,4-Diaminobenzene; 5-Amino-2-methylphenol | violet | A | 45 | faint beige |
| 3.20 | 2,4,5,6-Tetraaminopyrimidine sulfate; 5-Amino-2-methylphenol | blue | A | 20 | colorless |
| 3.21 | 2,5-Diamino-4-methylphenol dihydrochloride; 5-Amino-2-methylphenol | deep blue | A | 60 | faint gray |
| 3.22 | 1,4-Diamino-2-hydroxymethylbenzene; 5-Amino-2-methylphenol | beige | A | 60 | faint orange |
| 3.23 | 4-Amino-3-methylphenol; 2,4-Diamino-6-methylphenol | beige | A | 60 | faintly yellowish |
| 3.24 | 1,4-Diamino-2-methylbenzene sulfate; 3-Amino-2-methylphenol | brown | A | 60 | light brown |
| 3.25 | 4,5-Diamino-1-(2-hydroxyethyl)-1H-pyrazole; 3-(2-Hydroxyethyl)aminophenol | intensive red | B | 60 | faint rosé wine color |
| 3.26 | 4,5-Diamino-1-(2-hydroxyethyl)-1H-pyrazole; 5-(2-Hydroxyethyl)amino-2-methylphenol | intensive orange | B | 60 | faint orange |
| 3.27 | 4-Amino-3-methylphenol/ 5-Amino-2-ethylphenol | pinkish-orange | A | 20 | colorless |
| 3.28 | 4,5-Diamino-1-(2-hydroxyethyl)-1H-pyrazole; 2-Methyl-1-naphthol acetate | intensive pink | B | 60 | faint pink |
| 3.29 | 1,4-Diaminobenzene/ 1,3-Diaminobenzene | deep blue | A | 60 | beige |
| 3.30 | 1,4-Diamino-2-(2-hydroxyethyl) benzene sulfate/ 1,3-Diaminobenzene | deep blue | A | 20 | faintly yellowish |

TABLE 3-continued

Coloring and color removal results

| No. | Developer/coupler combination plus nitro dye(s) | Tint after dyeing | Stripper gel | Duration of stripping (in minutes) | Tint after color removal |
|---|---|---|---|---|---|
| 3.31 | 4-Amino-3-methylphenol (0.06%); 1-Naphthol (0.04%); 5-Amino-2-methylphenol (0.03%) | pinkish-red | A | 20 | colorless |

Example 4

Tinting Composition

| | |
|---|---|
| HC Blue No. 12 | 0.60 g |
| HC Red No. 13 | 1.00 g |
| Cetylstearyl alcohol | 1.30 g |
| Cetyltrimethylammonium chloride | 0.47 g |
| Ethoxylated castor oil (35 mol ethylene oxide) | 0.47 g |
| Water, fully desalinated to make up | 100.00 g |

The pH value of the tinting composition is adjusted to 5.5 to 6.5.

10 g of the above tinting composition are applied to the hair and distributed evenly using an artist's brush. After an action time of 30 minutes at 40° C., the hair is rinsed with lukewarm water and then dried. A reddish-violet color is obtained.

The colored hair is then treated with the above-described stripper b1 for 60 minutes at 40° C., then washed thoroughly with water and a shampoo and then dried.

The thus-treated hair virtually regains its original color.

Example 5 a. Enzymatically Oxidized Hair Coloring

| | |
|---|---|
| Stearyl alcohol polyglycol ether (= Steareth 20) | 1.40 g |
| Sodium sulfite | 1.10 g |
| Disodium ethylene diaminotetraacetate | 0.30 g |
| D-Glucose | 1.00 g |
| Glycerine | 1.00 g |
| Isopropanol | 5.00 g |
| 1,2-propanediol | 2.00 g |
| 1,4-diamino-2-methylbenzene sulfate | 0.025M |
| 5-amino-2-methylphenol | 0.025M |
| Glucose oxidase (EC 1.1.3.4) | 400 units |
| Peroxidase (EC 1.11.1.7) | 400 units |
| 0.1M Borate buffer (pH 8.5) to make | 100.00 g | b. Stripper Gel (per b6 in Example 1)

The above hair coloring composition is applied to bleached hair. After an action time of 60 minutes at room temperature (25° C.), the hair is washed and dried.

The deep-violet-colored hair is then treated for 20 minutes at 40° C. The hair is then washed thoroughly and dried. The hair virtually regains its original color.

Example 6
Two-component Stripper Emulsion

| Component 1: | |
|---|---|
| Cetylstearyl alcohol | 4.50 g |
| Cetyl acetate | 0.50 g |
| Dimethicone | 0.50 g |
| Cetyltrimethylammonium chloride | 0.65 g |
| Ascorbic acid | 6.00 g |
| Water, fully deionized, to make up | 94.00 g |
| Component 2: | |
| Ascorbic acid (in powder form) | 6.00 g |
| | 100.00 g |

Component 1 is mixed with component 2 immediately prior to use, and the pH value of the ready-to-use stripper preparation thus obtained is adjusted to 2.5 with a 2% aqueous NaOH solution.

Example 7
Stripper Gel

| | |
|---|---|
| 8.00 g | Ascorbic acid |
| 2.00 g | Hydroxyethylcellulose |
| 0.50 g | Silica |
| 0.16 g | Dipotassium hydrogen phosphate |

The mixture is added before use to 89.34 g of warm water and mixed well. The stripper gel thus obtained can be used to strip fibers or hair dyed with oxidative dyes.

The L*a*b color measurement values given in the present Examples were determined using a Minolta color measuring apparatus, of the type known as Chromameter II.

The L value stands for the lightness (that is, the lower the L value, the greater the intensity), while the a value is a measure of the red proportion (that is, the higher the a value, the higher the proportion of red). The b value is a measure for the blue component of the color; the proportion of blue is greater, the more negative the b value is.

The value D indicates the color difference that exists between the untreated strands and the dyed or stripped strands. It is determined as follows:

$$D = \sqrt{(L_i-L_0)^2 + (a_i-a_0)^2 + (b_i-b_0)^2}$$

in which $L_0$, $a_0$ and $b_0$ represent the color measurement values of untreated hair, and $L_i$, $a_i$ and $b_i$ represent the values of the treated hair. The stripping rate was ascertained as follows:

Stripping % = [1−(D after stripping/D after dyeing)]×100.

All the percentages given in the present application, unless otherwise noted, are weight percents.

What is claimed is:

1. An aqueous or aqueous-alcoholic reductive composition for reductively removing color from hair dyed with oxidative hair dye compounds, said reductive composition in the form of a gel, cream, emulsion, foam or solution and having a pH of from 1.8 to 6 and wherein said reductive composition consists essentially of:

water;

from 1 to 50% by weight of at least one reductone;

from 0.1 to 10% by weight of at least one thiol;

an amount of at least one pH adjusting agent sufficient for adjusting said pH to a predetermined value between 1.8 and 6, said at least one pH adjusting agent being selected from the group consisting phosphoric acid, acetic acid, glycolic acid, salicylic acid, glutathione, gluconic acid lactone, α-hydroxycarboxylic acids, alkanolamines, alkylamines, alkali hydroxides, ammonium hydroxide, alkali carbonates, ammonium carbonates and alkali phosphates; and at least one cosmetic additive selected from the group consisting of lower aliphatic alcohols, glycols, anionic surfactants, cationic surfactants, amphoteric surfactants, nonionic surfactants, thickeners, starch, cellulose derivatives, perfumes, hair conditioners, hair volumizers, preservatives, petrolatum, paraffin oils, cationic resins, fatty acids, cholesterol, pantothenic acid and betaine.

2. An aqueous or aqueous-alcoholic reductive composition for reductively removing color from hair dyed with oxidative hair dye compounds, said reductive composition in the form of a gel, cream, emulsion, foam or solution and having a pH of from 1.8 to 6 and wherein said reductive composition consists essentially of:

water;

from 1 to 50% by weight of at least one reductone;

from 0.1 to 10% by weight of at least one thiol;

from 0.001 to 5% by weight of at least one sulfite;

an amount of at least one pH adjusting agent sufficient for adjusting said pH to a predetermined value between 1.8 and 6, said at least one pH adjusting agent being selected from the group consisting phosphoric acid, acetic acid, glycolic acid, salicylic acid, glutathione, gluconic acid lactone, α-hydroxycarboxylic acids, alkanolamines, alkylamines, alkali hydroxides, ammonium hydroxide, alkali carbonates, ammonium carbonates and alkali phosphates; and at least one cosmetic additive selected from the group consisting of lower aliphatic alcohols, glycols, anionic surfactants, cationic surfactants, amphoteric surfactants, nonionic surfactants, thickeners, starch, cellulose derivatives, perfumes, hair conditioners, hair volumizers, preservatives, petrolatum, paraffin oils, cationic resins, fatty acids, cholesterol, pantothenic acid and betaine.

3. The composition as defined in claim 1 or 2, wherein said at least one reductone is selected from the group consisting of ascorbic acid, isoascorbic acid, salts of ascorbic acid, salts of isoascorbic acid, esters of ascorbic acid, esters of isoascorbic acid, hydroxypropanediol and 2,3-dihydroxy-2-cyclopenten-1-one.

4. The composition as defined in claim 1 or 2, wherein said at least one reductone is selected from the group consisting of ascorbic acid, isoascorbic acid, alkali metal ascorbates, alkaline earth metal ascorbates, alkali metal isoascorbates, alkaline earth metal isoascorbates, esters of ascorbic acid, esters of isoascorbic acid, hydroxypropanediol and 2,3-dihydroxy-2-cyclopenten-1-one.

5. The composition as defined in claim 1 or 2, wherein said at least one reductone is 6-O-palmitoyl ascorbate.

6. The composition as defined in claim 1 or 2, wherein said at least one reductone is ascorbic acid, isoascorbic acid or a mixture of said ascorbic acid and isoascorbic acid and is made in situ by reacting an acid with at least one member selected from the group consisting of alkali metal ascorbates, alkaline earth metal ascorbates, alkali metal isoascorbates and alkaline earth metal isoascorbates.

7. The composition as defined in claim 1 or 2, wherein said at least one thiol is selected from the group consisting of cysteine, salts of cysteine, N-acetyl cysteine, cysteamine, salts of cysteamine, mercapto-acetaldehyde, penicillamine, glutathione, homocysteine, salts of homocysteine and calcium thioglycolate.

8. The composition as defined in claim 2, wherein said at least one sulfite is an alkali sulfite or an alkaline earth sulfite.

9. The composition as defined in claim 1 or 2, containing from 2 to 5% by weight of said at least one thiol.

10. The composition as defined in claim 2, containing from 0.01 to 0.5% by weight of said at least one sulfite.

11. The composition as defined in claim 1 or 2, further comprising n-propanol and in the form of said solution.

12. A method for reductively removing color from hair dyed with oxidative hair dye compounds, said method consisting of the steps of:

a) providing an aqueous or aqueous-alcoholic reductive composition for removing color from hair dyed with oxidative hair dye compounds, said reductive composition being in the form of a gel, cream, emulsion, foam or solution and having a pH of from 1.8 to 6, and wherein said reductive composition consists essentially of water; a first combination of from 1 to 50% by weight of at least one reductone and from 0.1 to 10% by weight of at least one thiol or a second combination of from 1 to 50% by weight of at least one reductone, from 0.1 to 10% by weight of at least one thiol and from 0.001 to 5% by weight of at least one sulfite; an amount of at least one pH adjusting agent sufficient for adjusting said pH to a predetermined value between 1.8 and 6, said at least one pH adjusting agent being selected from the group consisting of phosphoric acid, acetic acid, glycolic acid, salicylic acid, glutathione, gluconic acid lactone, α-hydroxycarboxylic acids, alkanolamines, alkylamines, alkali hydroxides, ammonium hydroxides, alkali carbonates, ammonium carbonates and alkali phosphates; and at least one cosmetic additive selected from the group consisting of lower aliphatic alcohols, glycols, anionic surfactants, cationic surfactants, amphoteric surfactants, nonionic surfactants, thickeners, starch, celluose derivatives, perfumes, hair conditioners, hair volumizers, preservatives, petrolatum, paraffin-oils, cationic resins, fatty acids, cholesterol, pantothenic acid and betaine;

b) applying an effective amount of said aqueous or aqueous-alcoholic composition for reductively removing color to hair dyed with said oxidative hair dye compounds;

c) allowing the reductive composition applied in step b) to act on the hair for a period from 5 to 60 minutes at a temperature of 20 to 50° C.; and d) after the allowing of step c), rinsing the composition from the hair with water and washing the hair with a shampoo as needed and subsequently drying the hair.

13. The method as defined in claim 12, wherein said at least one reductone is selected from the group consisting of ascorbic acid, isoascorbic acid, salts of ascorbic acid, salts of isoascorbic acid, esters of ascorbic acid, esters of isoascorbic acid, hydroxypropanediol and 2,3-dihdyrdxy-2-cyclopenten-1-one.

14. The method as defined in claim 12, wherein said at least one thiol is selected from the group consisting of cysteine, salts of cysteine, N-acetyl cysteine, cysteamine, salts of cysteamine, mercapto-acetaldehyde, penicillamine, glutathione, homocysteine, salts of homocysteine and calcium thioglycolate.

15. The method as defined in claim 12, wherein said at least one sulfite is an alkali sulfite or an alkaline earth sulfate.

16. The method as defined in claim 12, wherein said composition for reductively removing the color contains from 2 to 5% by weight of said at least one thiol.

17. The method as defined in claim 12, wherein said composition for reductively removing the color contains from 0.01 to 0.5% by weight of said at least one sulfite.

18. A multicomponent kit for successively coloring hair and reductively removing color from dyed hair, said multi-componoent kit consisting of a first part and a second part;

wherein said first part consists of a composition for oxidative dyeing of hair, and said second part consists of a reductive composition for reductive removal of color from dyed hair, said second composition having a pH value of from 1.8 to 6 and consisting essentially of:

water;

from 1 to 50% by weight of at least one reductone;

from 0.1 to 10% by weight of at least one thiol;

an amount of at least one pH adjusting agent sufficient for adjusting said pH to a predetermined value between 1.8 and 6, said at least one pH adjusting agent being selected from the group consisting phosphoric acid, acetic acid, glycolic acid, salicylic acid, glutathione, gluconic acid lactone, $\alpha$-hydroxycarboxylic acids, alkanolamines, alkylamines, alkali hydroxides, ammonium hydroxide, alkali carbonates, ammonium carbonates and alkali phosphates; and at least one cosmetic additive selected from the group consisting of lower aliphatic alcohols, glycols, anionic surfactants, cationic surfactants, amphoteric surfactants, nonionic surfactants, thickeners, starch, cellulose derivatives, perfumes, hair conditioners, hair volumizers, preservatives, petrolatum, paraffin oils, cationic resins, fatty acids, cholesterol, pantothenic acid and betaine.

19. A multicomponent kit for successively coloring hair and reductively removing color from dyed hair, said multi-componoent kit consisting of a first part and a second part;

wherein said first part consists of a composition for oxidative dyeing of hair, and said second part consists of a reductive composition for reductive removal of color from dyed hair, said second composition having a pH value of from 1.8 to 6 and consisting essentially of:

water;

from 1 to 50% by weight of at least one reductone;

from 0.1 to 10% by weight of at least one thiol;

from 0.001 to 5% by weight of at least one sulfite;

an amount of at least one pH adjusting agent sufficient for adjusting said pH to a predetermined value between 1.8 and 6, said at least one pH adjusting agent being selected from the group consisting phosphoric acid, acetic acid, glycolic acid, salicylic acid, glutathione, gluconic acid lactone, $\alpha$-hydroxycarboxylic acids, alkanolamines, alkylamines, alkali hydroxides, ammonium hydroxide, alkali carbonates, ammonium carbonates and alkali phosphates; and at least one cosmetic additive selected from the group consisting of lower aliphatic alcohols, glycols, anionic surfactants, cationic surfactants, amphoteric surfactants, nonionic surfactants, thickeners, starch, cellulose, hydroxymethyl cellulose derivatives, perfumes, hair conditioners, hair volumizers, preservatives, petrolatum, paraffin oils, cationic resins, fatty acids, cholesterol, pantothenic acid and betaine.

20. The multicomponent kit as defined in claim 18 or 19, wherein said composition for oxidative dyeing of the hair in said first part includes dye precursors that form an oxidative dye on addition of an oxidizing agent.

21. The multicomponent kit as defined in claim 18 or 19, wherein said composition for oxidative dyeing of hair in said first part includes at least one direct dye and dye precursors that form an oxidative dye on addition of an oxidizing agent.

* * * * *